(12) United States Patent
Fernholz et al.

(10) Patent No.: US 10,323,797 B2
(45) Date of Patent: Jun. 18, 2019

(54) PRODUCT YIELD LOSS MANAGEMENT

(71) Applicant: Ecolab USA Inc., Saint Paul, MN (US)

(72) Inventors: Peter J. Fernholz, Burnsville, MN (US); Anthony Erickson, Golden Valley, MN (US); Rodney H. Banks, Aurora, IL (US)

(73) Assignee: Ecolab USA Inc., Saint Paul, MN (US)

( * ) Notice: Subject to any disclaimer, the term of this patent is extended or adjusted under 35 U.S.C. 154(b) by 132 days.

(21) Appl. No.: 14/283,785

(22) Filed: May 21, 2014

(65) Prior Publication Data

US 2015/0338026 A1 Nov. 26, 2015

(51) Int. Cl.
*B08B 3/00* (2006.01)
*F17D 3/01* (2006.01)
(Continued)

(52) U.S. Cl.
CPC ............... *F17D 3/01* (2013.01); *F17D 1/14* (2013.01); *G01N 21/64* (2013.01); *G01N 21/85* (2013.01);
(Continued)

(58) Field of Classification Search
CPC ......... Y10T 137/0419; Y10T 137/0424; Y10T 137/4259
(Continued)

(56) References Cited

U.S. PATENT DOCUMENTS 3,350,301 A  10/1967 Hoffman
5,386,927 A * 2/1995 Janssen ................ B08B 9/0321
                                                137/240
(Continued)

FOREIGN PATENT DOCUMENTS

| CN | 102939529 A | 2/2013 |
|---|---|---|
| CN | 103630639 A | 3/2014 |
| EP | 2684462 A2 | 1/2014 |
| WO | 01/38218 A1 | 5/2001 |
| WO | 2013165999 A1 | 11/2013 |

OTHER PUBLICATIONS

U.S. Appl. No. 14/039,683, filed Sep. 27, 2013, entitled, "Multi-Channel Fluorometric Sensor and Method of Using Same," 69 pages.

(Continued)

*Primary Examiner* — Robert K Arundale
(74) *Attorney, Agent, or Firm* — Fredrikson & Byron, P.A.

(57) ABSTRACT

During the production of consumable liquids such as milk, soup, and juice, the liquid consumable may be transferred from one location to another location through a fluid conduit. For example, a consumable liquid may be transferred from a storage tank to another destination through piping. At the end of the process, the piping may be purged with a flushing fluid to push the liquid consumable remaining in the piping to the end destination, thus preventing the volume of liquid remaining in the piping from being wasted. To control the flushing processing, fluid flowing through the piping may be fluorometrically analyzed to determine a concentration of product in the fluid. The flushing liquid can then be controlled based on the determined concentration. For example, the supply of flushing liquid may be terminated when the concentration of product falls below a threshold, indicating the flushing liquid is diluting the liquid consumable.

17 Claims, 6 Drawing Sheets

(51) Int. Cl.
*F17D 1/14* (2006.01)
*G01N 21/64* (2006.01)
*G05B 7/00* (2006.01)
*G01N 21/85* (2006.01)

(52) U.S. Cl.
CPC ....... *G05B 7/00* (2013.01); *G01N 2021/6497* (2013.01); *Y10T 137/034* (2015.04); *Y10T 137/0329* (2015.04); *Y10T 137/0424* (2015.04); *Y10T 137/2509* (2015.04)

(58) Field of Classification Search
USPC .................................. 250/273–576; 356/951
See application file for complete search history.

(56) References Cited

U.S. PATENT DOCUMENTS

| | | | | |
|---|---|---|---|---|
| 5,658,798 | A | * | 8/1997 | Bertin .................... G01N 33/02 436/172 |
| 5,876,960 | A | | 3/1999 | Rosen |
| 5,990,486 | A | * | 11/1999 | Chen ..................... G05D 11/138 250/573 |
| 6,197,739 | B1 | | 3/2001 | Oakes et al. |
| 6,240,952 | B1 | * | 6/2001 | Schroeder ............ B08B 9/0325 134/169 R |
| 6,314,981 | B1 | * | 11/2001 | Mayzou .................... F17C 6/00 137/15.04 |
| 6,423,152 | B1 | * | 7/2002 | Landaas ................ B08B 9/0325 134/10 |
| 7,247,210 | B2 | | 7/2007 | Staub et al. |
| 7,550,746 | B2 | | 6/2009 | Tokhtuev et al. |
| 7,614,410 | B2 | | 11/2009 | Kenowski et al. |
| 8,373,140 | B2 | | 2/2013 | Tokhtuev et al. |
| 8,614,793 | B2 | | 12/2013 | Tokhtuev et al. |
| 2004/0025606 | A1 | * | 2/2004 | Veenstra ................. A01J 5/007 73/865.9 |
| 2004/0118432 | A1 | * | 6/2004 | Kenowski ............ B08B 9/0325 134/18 |
| 2005/0183744 | A1 | | 8/2005 | Staub et al. |
| 2005/0184008 | A1 | | 8/2005 | Schacht et al. |
| 2006/0046945 | A1 | | 3/2006 | Herdt et al. |
| 2006/0286676 | A1 | | 12/2006 | Van Camp et al. |
| 2007/0241037 | A1 | | 10/2007 | Wang |
| 2008/0105279 | A1 | | 5/2008 | Herdt et al. |
| 2008/0105282 | A1 | | 5/2008 | Fernholz et al. |
| 2010/0003381 | A1 | | 1/2010 | Smith |
| 2011/0260079 | A1 | | 10/2011 | Tokhtuev et al. |
| 2013/0293881 | A1 | | 11/2013 | Tokhtuev et al. |
| 2014/0261550 | A1 | | 9/2014 | Erickson et al. |
| 2014/0373930 | A1 | * | 12/2014 | Luedtke ................ B08B 9/0323 137/15.05 |
| 2015/0090900 | A1 | * | 4/2015 | Banks .................... G01N 21/53 250/432 R |

OTHER PUBLICATIONS

International Patent Application No. PCT/US2015/031597, International Search Report and Written Opinion dated Sep. 1, 2015, 9 pages.
European Patent Application No. 15796629.2, Extended European Search Report dated Jan. 3, 2018, 8 pages.

* cited by examiner

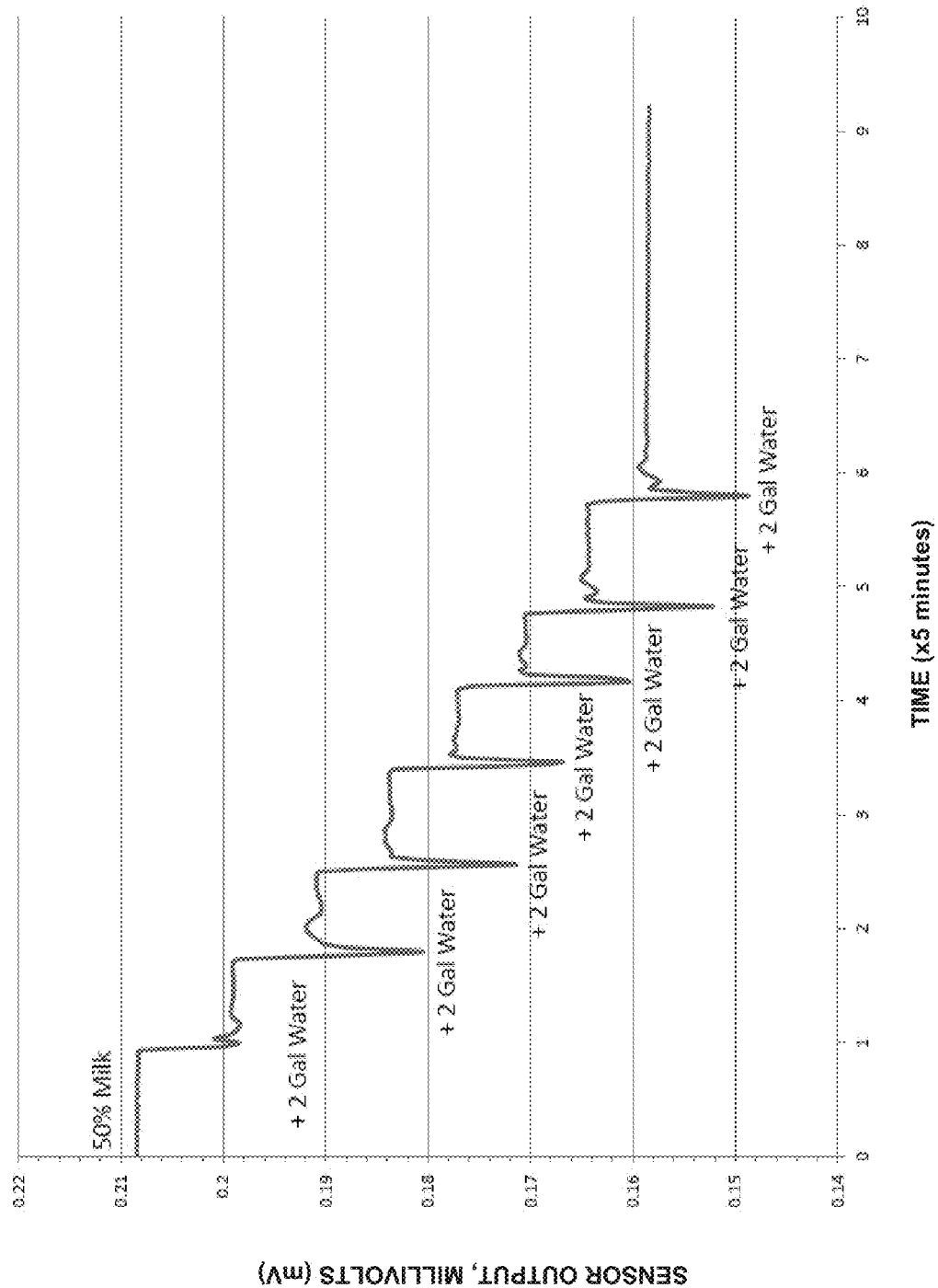

PRODUCT YIELD LOSS MANAGEMENT

TECHNICAL FIELD

This disclosure relates to fluid monitoring and control and, more particularly, to fluid monitoring and control for product yield loss management.

BACKGROUND

Within the food and beverage industry, a variety of liquid products and intermediate liquids may be conveyed through a production facility before being packaged and delivered to an end consumer. In the dairy industry, for example, liquid milk is harvested from animals and typically transported by tanker truck to a local dairy plant. Upon arriving at the dairy plant, the milk is unloaded from the tanker truck and sent either to processing or storage. During processing, the milk may be separated into cream and skimmed milk, evaporated, pasteurized, homogenized, or otherwise processed to produce a number of desired dairy products. In some cases, the processed milk is sent to a filling station at the end of the production process where the milk is dispensed into consumer-sized containers suitable for sale in a grocery store or other retail location.

Throughout the production process, raw milk and its derivatives (e.g., cream, skimmed milk) may be transported between different storage reservoirs and processing equipment through piping extending throughout the dairy plant. At the end of a transfer process when most of the liquid being moved from one location to another location is complete, a flushing liquid may be chased through the piping to push any residual product in the piping to the destination location. For example, water may be flushed through the piping to push raw milk through the piping to the destination location, increasing yield by recovering the volume of milk otherwise remaining in the piping at the end of the transfer.

Current practice in dairy plants is typically to flush piping with water for a set period of time and cease flushing when the time is reached. The time is generally intended to be long enough to flush most residual milk product through the piping without sending an excessive amount of water to the destination location. Some amount of water may be tolerated in the final product as long as the water does not excessively dilute the product. Any milk product remaining in the piping after the flush is terminated is usually disposed.

In practice, the target flushing time for a particular length of piping may not maximize product recovery from the piping while preventing over dilution of the product. For example, the appropriate flushing time may vary as the length of the piping changes, the composition of the product being flushed changes, and/or the composition of the flushing liquid changes. Further, even when the target flushing time is appropriate, operator distraction may prevent adherence to the target flushing time.

SUMMARY

In general, this disclosure relates to fluid monitoring and the control of flushing liquid based on a monitored characteristic of the fluid. During the manufacture and processing of various liquid products, the liquid products may be conveyed from one location at a processing facility to another location through fluid conduits and also through various pieces of processing equipment. For example, in the food and beverage industry, a liquid product intended for human consumption may, at different times, be held in a storage tank, passed through an evaporator and/or reactor, conveyed through a bottling or filling station, and otherwise moved around the processing facility through fluid conduits. When transferring a batch of liquid between locations at a processing facility, residual liquid typically remains in the fluid transfer lines at the end of the transfer process. This can occur when a pump transferring the batch of liquid runs out of source liquid to draw into the pump and discharge under pressure through the fluid transfer lines to a downstream destination location. To help prevent the residual liquid remaining in the fluid transfer lines from being wasted, a flushing liquid may be pushed through the fluid transfer lines following the product liquid being conveyed to the downstream destination location. The flushing liquid may push product liquid remaining in the fluid transfer lines at the end of the transfer process toward the downstream destination location, increasing recovery of the product liquid.

To help control the flushing liquid, fluid passing through a fluid transfer line may be fluorometrically analyzed to determine a concentration of product in the fluid. For example, if the downstream destination location is a storage tank or piece of processing equipment, fluid may be extracted from a fluid transfer line adjacent the downstream destination location and fluorometrically analyzed to determine the concentration of product in the fluid before it reaches the destination location. Upon initiating the flush process, the liquid being pushed into the downstream destination location may be composed entirely of the product liquid remaining in the fluid transfer time. As the flushing liquid continues to push residual product liquid through the transfer line, the liquid being pushed into the downstream destination location may show a progressively decreasing concentration of the product liquid and a progressively increasing concentration of flushing liquid until the liquid flowing into the destination location is composed entirely of flushing liquid.

To prevent too much flushing liquid from flowing into the downstream destination location (or, in other examples, any flushing liquid), the liquid flowing into the downstream destination location can be fluorometrically analyzed to determine a concentration of product liquid in the fluid flow. For example, light can be emitted into the fluid to cause organic molecules in the fluid to generate fluorescent emissions. The magnitude and/or wavelength of the fluorescent emissions may correspond to the concentration of the product in the fluid. In some examples, the flow of flushing liquid is terminated when the fluorometrically determined concentration of the product liquid flowing into the downstream destination location falls below a threshold concentration. This can indicate that the flushing liquid, if allowed to continue to flow, may excessively dilute the product liquid.

In one example, a method is described that includes flushing a product liquid through a fluid conduit with a flushing liquid. The method includes fluorometrically analyzing fluid flowing through the fluid conduit to determine a concentration of product in the fluid and controlling the flushing liquid based on the determined concentration of the product in the fluid.

In another example, a system is described that includes a fluid reservoir, a source of product liquid, a source of flushing liquid, an optical sensor, and a controller. The fluid reservoir has an inlet configured to be connected to a fluid conduit. The source of product liquid is configured to be conveyed through the fluid conduit and into the fluid reservoir via the inlet. The source of flushing liquid is configured to be conveyed through the fluid conduit following the product liquid. The optical sensor is configured to fluorometrically analyze fluid flowing through the fluid conduit. The controller is configured to receive fluorometric data from the optical sensor and determine therefrom a concentration of product in the fluid, and control the flushing liquid based on the determined concentration of the product in the fluid.

The details of one or more examples are set forth in the accompanying drawings and the description below. Other features, objects, and advantages will be apparent from the description and drawings, and from the claims.

BRIEF DESCRIPTION OF DRAWINGS

FIG. 6 is a plot showing example optical response of an increasingly diluted milk solution.

DETAILED DESCRIPTION

The disclosure generally relates to fluorometric monitoring of a fluid flow that includes residual product liquid being pushed by a flushing liquid, allowing the residual product liquid to be captured for subsequent use or sale rather than disposed. Initially, product liquid is passed through a fluid conduit to a downstream destination location. A pump or other fluid pressurization device may be used to pressurize the product liquid and convey the liquid from an origin location to the destination location. When a suitable volume of product liquid has been conveyed to the destination location, the fluid pressurization device can stop delivering additional product liquid to the destination location. This can leave the fluid conduit extending between the origin location and the destination location filled with residual product liquid.

To evacuate the fluid conduit of the residual product liquid, a flushing liquid is passed through the fluid conduit. The flushing liquid may be a liquid having a different composition than the product liquid residing in the fluid conduit. The flushing liquid may enter the fluid conduit at or adjacent the origin location and be directed toward the destination location. The force of the incoming flushing liquid can push the residual product liquid in the fluid conduit toward the destination location, evacuating the conduit of the product liquid.

In some examples, the liquid flowing through the fluid conduit under the force of pressurized flushing liquid is fluorometrically analyzed to determine a concentration of the product liquid in the overall flow of liquid. The product liquid may emit fluorescent emissions in response to receiving appropriate wavelengths of light while the flushing liquid may not emit fluorescent emissions at these wavelengths. Alternatively, the product liquid may not emit fluorescent emissions while the flushing liquid emits fluorescent emissions. In either case, a concentration of the product liquid in a mixed sample containing both product liquid and flushing liquid can be determined based on the magnitude and/or wavelength of the fluorescent emissions emitted from the sample. For example, molecules naturally present in the product liquid may fluoresce in response to emitted light, allowing the concentration of the product liquid to be quantified without adding an artificial fluorescent tracer molecule to the fluid. With knowledge of the concentration of the product liquid in the fluid passing through the conduit, the fluid conduit can be flushed until the concentration falls below a threshold level. This threshold level may indicate that a suitable amount of product liquid has been recovered from the fluid conduit and, if the flushing liquid is not stopped or diverted, continued flushing may dilute the product liquid below a desired concentration.

Figure 1:
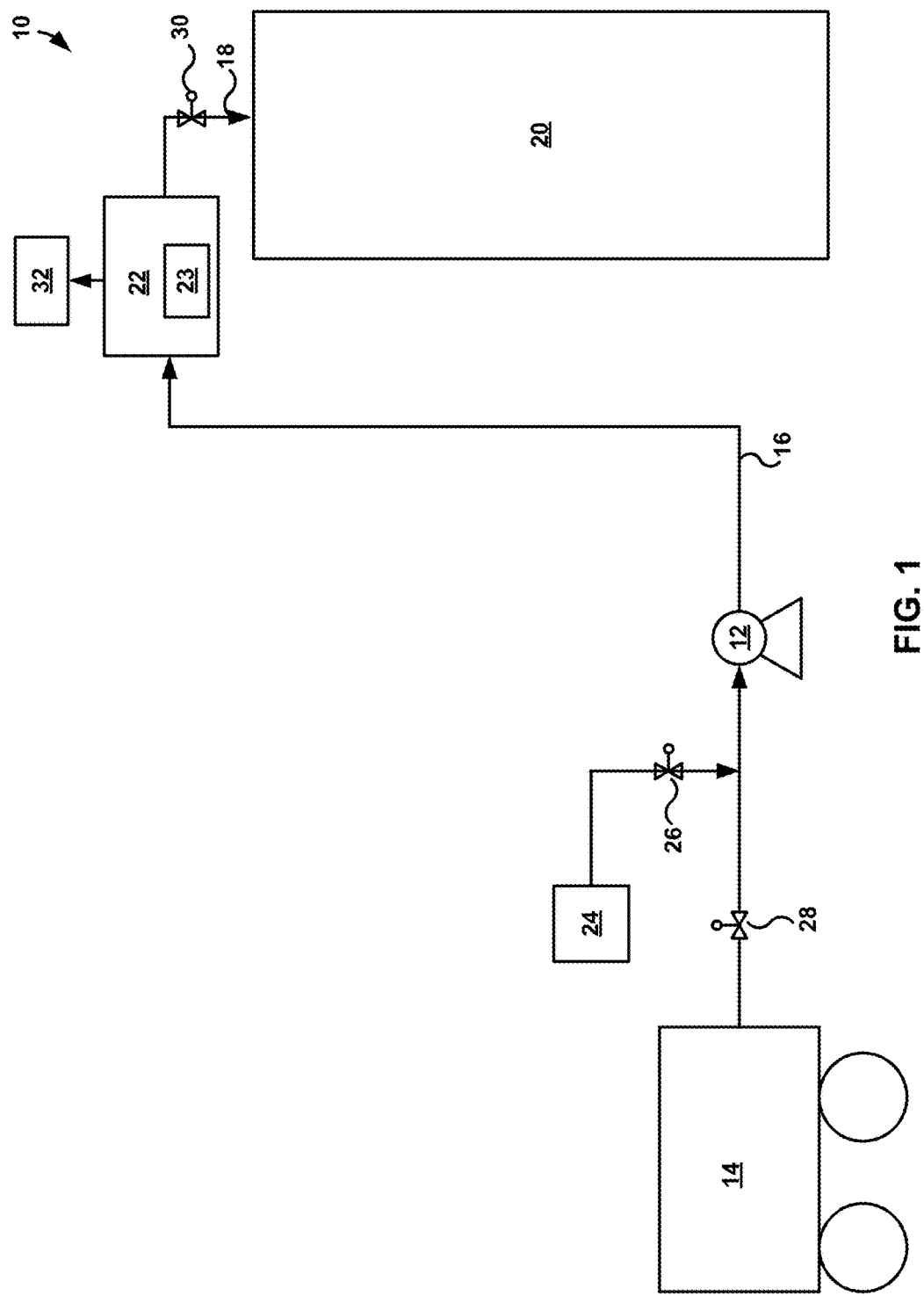
FIG. 1 is an illustration of an example system in which fluid can be fluorometrically analyzed to control a flushing operation.

FIG. 1 is an illustration of an example system 10 in which a product liquid is conveyed through processing equipment followed by a flushing liquid to flush residual product liquid from the equipment. System 10 includes a fluid pressurization device 12 (also referred to herein for purposes of illustration as "pump 12") fluidly connected to a source of product liquid 14. Pump 12 draws product liquid 14 at a suction side of the pump, pressurizes the fluid inside of the pump, and discharges the fluid at an elevated pressure into fluid conduit 16. Fluid conduit 16 is connected to an inlet 18 of a fluid reservoir 20 and conveys pressured fluid from the pump to the reservoir. Fluid reservoir 20 can receive product liquid 14 and hold the liquid, for example, to be used in subsequent processing steps, to be packaged, to be sold, or the like. An optical sensor 22 receives fluid flowing through conduit 16 and optically analyzes the fluid, e.g., to determine a concentration of product liquid in the flow of fluid. Optical sensor 22 is illustrated as being positioned before inlet 18 of fluid reservoir 20 such that the optical sensor can determine the concentration of product liquid in the fluid flowing through conduit 16 before the fluid enters the reservoir.

System 10 in FIG. 1 also includes a source of flushing liquid 24 fluidly connected to fluid reservoir 20 via pump 12 and fluid conduit 16. During operation of system 10, product liquid may be conveyed from the source of product liquid 14 through conduit 16 to fluid reservoir 20. Pump 12 may operate to transfer product liquid from the source 14 to fluid reservoir 20 until, for example, the source is substantially empty and/or the reservoir is full with a desired amount of product liquid. At this point during operation, pump 12 may cease operating, leaving fluid conduit 16 filled with residual product liquid. To help prevent the residual product liquid remaining in fluid conduit 16 from being waste, pump 12 may begin drawing flushing liquid from flushing liquid source 24 and pumping the flushing liquid through fluid conduit 16 toward fluid reservoir 20. The force of pressurized flushing liquid moving through fluid conduit 16 can push the residual product liquid in fluid conduit 16 toward and into fluid reservoir 20. In this way, fluid liquid 24 can help increase the recovery or yield of product transferred from source 14 to reservoir 20.

System 10 is illustrated as including an assortment of valves (26, 28, 30) and fluid conduits that control fluid movement through the system. A controller 32 manages the overall operation of system 10. Controller 32 may be communicatively coupled to various components within system 10, for example via a wired or wireless connection, so as to send and receive electronic control signals and information between controller 32 and the communicatively coupled components. For example, controller 32 may electronically actuate valves (26, 28, 30) to open/close the valves and control pump 12 to control fluid movement through the system. Controller 32 can also control optical sensor 22 to optically analyze fluid moving through the system and determine a concentration of product therein.

Although FIG. 1 illustrates one particular arrangement of a system in which fluid is fluorometrically analyzed to control a flushing liquid, it should be understood that this is only one example. The disclosure is not limited to a system having any particular configuration, much less the particular configuration of FIG. 1. In different examples, system 10 may not include pump 12 but may instead convey liquid from pressurized fluid sources, such as when the source of product liquid 14 is a pressurized tanker truck and the source of flushing liquid 24 is water from a pressurized water main. As another example, fluid conduit 16 in system 10 may not be connected to fluid reservoir 20 but may instead be connected to a different piece of process equipment, such as an evaporator, condenser, packaging station, or yet other type of process equipment. System 10 can include additional or different features, as will be appreciated by those of ordinary skill in the art.

System 10 can be implemented to help control the processing of any desired product liquids. Exemplary industries that may use system 10 include the food industry, the beverage industry, the pharmaceutical industry, the chemical industry, and the water purification industry. In the case of the food and beverage industry, product liquid 14 being processed in system 10 and conveyed through fluid conduit 16 can include, but is not limited to, dairy products such as raw milk, whole and skimmed milk, condensed milk, cream, whey and whey derivatives, buttermilk, lactose solutions, and lactic acid; protein solutions such as soya protein isolate, soya whey, nutrient yeast and fodder yeast, and whole egg; fruit juices such as orange and other citrus juices, apple juice and other pomaceous juices, red berry juice, coconut milk (e.g., condensed coconut milk), and tropical fruit juices; vegetable juices such as tomato juice, beetroot juice, carrot juice, and grass juice; starch products such as glucose, dextrose, fructose, isomerose, maltose, starch syrup, and dextrine; sugars such as liquid sugar, white refined sugar, sweetwater, and insulin; extracts such as coffee and tea extracts, hop extract, malt extract, yeast extract, pectin, and meat and bone extracts; hydrolyzates such as whey hydrolyzate, soup seasonings, milk hydrolyzate, and protein hydrolyzate; fermented beverages such alcoholic beer and liquor, de-alcoholized beer, and wort; baby food (e.g., infant formula), egg whites, liquid egg, lycene for animal feed, polyols, bone oils, and condensed meat bullion and powders.

In some examples, the product liquid 14 includes a polycyclic compound and/or a benzene molecule that has one or more substituent electron donating groups such as, e.g., —OH, —NH2, and —OCH3, which may exhibit fluorescent characteristics. These molecules may be naturally present within product liquid 14 and may emit fluorescent emissions in response to receiving an appropriate wavelength of light. For example, product liquid 14 may contain fluorescing molecules that are formed during the cultivation and/or growth of the product liquid, or a precursor thereto, and are not artificially added for purposes of providing a fluorescent tracer.

In general, flushing liquid 24 may be a fluid that functions to flush equipment (e.g., fluid conduit 16) within system 10 and displaces product liquid 14 remaining in the equipment. This can help recover residual product liquid trapped within the process equipment by pushing it to a downstream location (e.g., fluid reservoir 20) and also prepare the equipment to process a subsequent batch of fluid. Flushing liquid 24 can be any liquid having a different composition than that of product liquid 14. In one example, flushing fluid 24 is water (e.g., may consist, or consist essentially of, water). When flushing fluid 24 is water, the water may be supplied as fresh water from a pressurized water main or other suitable source. In other examples, flushing liquid 24 may contain the same chemical compounds as product liquid 24 but in a different concentration than is present in the product liquid. For example, in instances where product liquid 14 is a dairy product (e.g., cream, whole milk), the flushing liquid 24 may be another dairy product (e.g., skim milk, 1% milk) having a different concentration of fat and/or protein than the product liquid.

During operation of system 10, controller 32 may receive a request requesting that product liquid be transferred from the source 14 to fluid reservoir 20. In response to the request, controller 32 can control system 10 to place product liquid source 14 in fluid communication with fluid reservoir 20. For example, controller 32 can open valves 28 and 30 and activate pump 12 to draw product liquid from the source and push pressurized product liquid through fluid conduit 16 into fluid reservoir 20. Pump 12 may continuously pump product liquid from the source 14 to fluid reservoir 20 until a suitable amount of product liquid has been transferred through fluid conduit 16. This may occur when the product liquid source 14 is substantially or entirely empty. This may also occur when a desired amount of product liquid has been added to fluid reservoir 20. In either case, controller 32 may close valves 28 and/or 30 and stop pump 12 after transferring a suitable amount of product liquid from source 14 to reservoir 20. At this point, fluid conduit 16 may be partially or entirely filled with residual product liquid. The residual product liquid may be static (e.g., non-moving) and trapped/held within fluid conduit 16 between source 14 and reservoir 20.

With the transfer of product liquid complete, controller 32 may initiate a flush process by opening valves 26 and/or 30 and further activating pump 12 to draw flushing liquid from the source and push the pressurized flushing liquid through fluid conduit 16. The pressurized flushing fluid may push residual product fluid inside of fluid conduit 16 into fluid reservoir 20 as the flushing liquid advances toward the reservoir 20. When a target amount of flushing has occurred, for example as discussed in greater detail below, controller 32 may close valves 26 and/or 28 and stop pump 12. This can prevent an excessive amount of flushing liquid from being introduced into fluid reservoir 20. Alternatively, in other configurations of system 10 beyond that shown in FIG. 1, controller 32 may close valve 30 and/or open another valve to divert flushing liquid away from fluid reservoir 20, such as to a drain. In this manner, controller 32 can control the transfer of product liquid and flushing liquid through fluid conduit 16 in system 10.

While transfer of product liquid from source 14 and also flushing liquid from source 24 to fluid reservoir 20 has been described as being executed under the control of controller 32, it should be appreciated that some or all of the transfer steps may be manually performed by an operator. For example, the operation of pump 12 and the opening and closing of valves (26, 28, 30) within system 10 may be performed by a human operator in addition to or in lieu of controller 32.

System 10 includes optical sensor 22. Optical sensor 22 is configured to optically analyze fluid passing through fluid conduit 16 and into fluid reservoir 20. As discussed in greater detail with respect to FIG. 2, optical sensor 22 may receive a sample of the fluid flowing through fluid conduit 16, direct light into the fluid to generate fluorescent emissions from product liquid (if any) in the fluid, and detect the fluorescent emissions emitted by the fluid. The fluorescent emissions may be proportional to the concentration of product liquid in the fluid. Accordingly, controller 32 may determine a concentration of a product (e.g., product liquid) in the fluid based on data generated by optical sensor 22. Controller 32 may further control the flushing process based on the determined concentration of product liquid in the fluid flowing into fluid reservoir 20.

Optical sensor 22 may be implemented in a number of different ways in system 10. In the example shown in FIG. 1, optical sensor 22 is positioned in-line with fluid conduit 16 adjacent inlet 18 of fluid reservoir 20. When so positioned, optical sensor 22 can determine the concentration of the fluid flowing through fluid conduit 16, e.g., shortly before the fluid discharges into fluid reservoir 20. In other examples, a sample line may be connected to a main conduit connected to fluid reservoir 20. In such examples, the sample line can fluidly connect optical sensor 22 to the main fluid conduit. As fluid moves through the main fluid conduit, a portion of the fluid may enter the sample line and pass adjacent an optical sensor head of the sensor, thereby allowing optical sensor 22 to determine a concentration of fluorescing product in the fluid flowing through the main fluid conduit. When implemented to receive fluid continuously, optical sensor 22 may be characterized as an online optical sensor. In other examples, optical sensor 22 may be implemented as an offline optical sensor that receives fluid on an intermittent basis, e.g., by manually filling the optical sensor with fluid.

As briefly mentioned above, optical sensor 22 is illustrated as being positioned before inlet 18 of fluid reservoir 20. Such a position can be useful to optically determine the concentration of a product in liquid flowing through fluid conduit 16 shortly before the fluid is discharged into fluid reservoir 20. If the concentration of product in the fluid falls outside of the desired concentration window, fluid flow can be stopped or diverted rather than discharging the fluid into fluid reservoir 20. In various examples, optical sensor 22 may be positioned less than 20 feet away from inlet 18 of fluid reservoir 10, such as less than 10 feet, less than 5 feet, or less than 2 feet. In applications where optical sensor 22 is fluidly connected to fluid conduit 16 via a sample line, the sample line may extract liquid from the main fluid conduit at a location within any of these foregoing distances.

In one example, optical sensor 22 receives fluid flowing through fluid conduit 16 as pressurized flushing fluid is passing through the conduit toward fluid reservoir 20. Optical sensor 22 optically analyzes the fluid by directing light into the fluid to cause fluorescing molecules in the fluid to excite and emit fluorescent energy. The fluorescing molecules may be molecules present in the product fluid but not present in the flushing fluid or present in the flushing fluid in a lower concentration than in the product fluid. Optical sensor 22 detects the fluorescent energy and generates therefrom an optical sensor output proportional to the amount and/or wavelength of the fluorescent energy detected. Controller 32 can receive the optical sensor output and determine a concentration of product in the fluid based on the output. For example, controller 32 may determine a concentration of product liquid in the fluid (e.g., where the fluid contains a mixture of product liquid and flushing liquid) and/or a concentration of a specific molecule in the fluid (e.g., protein) that is associated with the product liquid. From this information, controller 32 may control the flushing fluid, for example, by increasing or decreasing the rate at which pump 12 pumps the fluid through fluid conduit 16, stopping pump 12, and/or closing valves 26 and/or 30 to prevent excessive flushing fluid from being directed into fluid reservoir 20.

Upon initiating the flush process by drawing liquid from flushing liquid source 24 and pumping the liquid toward fluid reservoir 20, the liquid being pushed through inlet 18 of the reservoir may be composed substantially entirely of the product liquid. This may be the residual product liquid held in fluid conduit 16 prior to initiating the flush process. As the flushing liquid continues to push residual product liquid through inlet 18 of fluid reservoir 20, the liquid being pushed into the reservoir may exhibit a decreasing concentration of the product liquid and an increasing concentration of flushing liquid. This may occur when the interface between the product liquid and the flushing liquid reaches inlet 18 of fluid reservoir 20. The interface between the product liquid and the flushing liquid may be a region where the product liquid and flushing liquid are intermixed, which may also be referred to as a region of phase separation between the product liquid and the flushing liquid. If flushing liquid were to continue flowing through fluid conduit 16 and into fluid reservoir 20, the liquid being pushed through inlet 18 of reservoir 20 may continue decreasing in concentration of product liquid until the fluid is composed substantially entirely of the flushing liquid. By determining the concentration of product liquid in the flow of fluid being pushed into fluid reservoir 20, controller 32 can stop directing flushing liquid toward the reservoir, e.g., when the concentration of the product liquid falls below an acceptable threshold.

Fluid conduit 16 in FIG. 1 is illustrated as connecting product liquid source 14 and flushing liquid source 24 to fluid reservoir 20. Product liquid source 14 may be implemented using any equipment suitable for supplying product liquid to a downstream destination location. In different examples, product liquid source 14 may be a fixed tank, a mobile tanker truck, a bottle, a tote, a reactor vessel, an evaporator, a condenser, or other type of equipment capable of supplying product liquid. Similarly, fluid reservoir 20 may be any type of container designed to receive and hold liquid, such as a fixed tank, a mobile tanker truck, a bottle, a tote. In some examples, fluid reservoir 20 is configured to both receive product liquid and further process the product liquid. For example, fluid reservoir 20 may be part of a filling station (e.g., bottle filler) having one or more filling heads. As another example, fluid reservoir 20 may be a reactor vessel, distillation column, or other piece of processing equipment designed to both receive and process product liquid. In these examples, fluid reservoir 20 may receive and hold product liquid for a comparatively short period of time as the product liquid is being further processed.

Accordingly, although FIG. 1 illustrates one particular arrangement of a system in which fluid is fluorometrically analyzed to control a flushing liquid, it should be understood that the hardware and techniques of the disclosure may be beneficially implemented in systems beyond that of FIG. 1. For example, the hardware and techniques may be implemented in any system where one liquid comprises molecules that naturally fluoresce and is pushing or being pushed by another liquid that does not fluoresce or fluoresces to a different extent.

Pump 12 in system 10 may be any suitable fluid pressurization device such as a direct lift pump, positive displacement pump, velocity pump, buoyancy pump and/or gravity pump or any combination thereof. In other examples, system 10 does not include a pump. In general, components described as valves (26, 28, 30) may be any device that regulates the flow of a fluid by opening or closing fluid communication through a fluid conduit. In various examples, a valve may be a diaphragm valve, ball valve, check valve, gate valve, slide valve, piston valve, rotary valve, shuttle valve, and/or combinations thereof. Each valve may include an actuator, such as a pneumatic actuator, electrical actuator, hydraulic actuator, or the like. For example, each valve may include a solenoid, piezoelectric element, or similar feature to convert electrical energy received from controller 32 into mechanical energy to mechanically open and close the valve. Each valve may include a limit switch, proximity sensor, or other electro-mechanical device to provide confirmation that the valve is in an open or closed position, the signals of which are transmitted back to controller 32.

Fluid conduits and fluid lines in system 10 may be pipes or segments of tubing that allow fluid to be conveyed from one location to another location in the system. The material used to fabricate the conduits should be chemically compatible with the liquid to be conveyed and, in various examples, may be steel, stainless steel, or a polymer (e.g., polypropylene, polyethylene).

Figure 2:
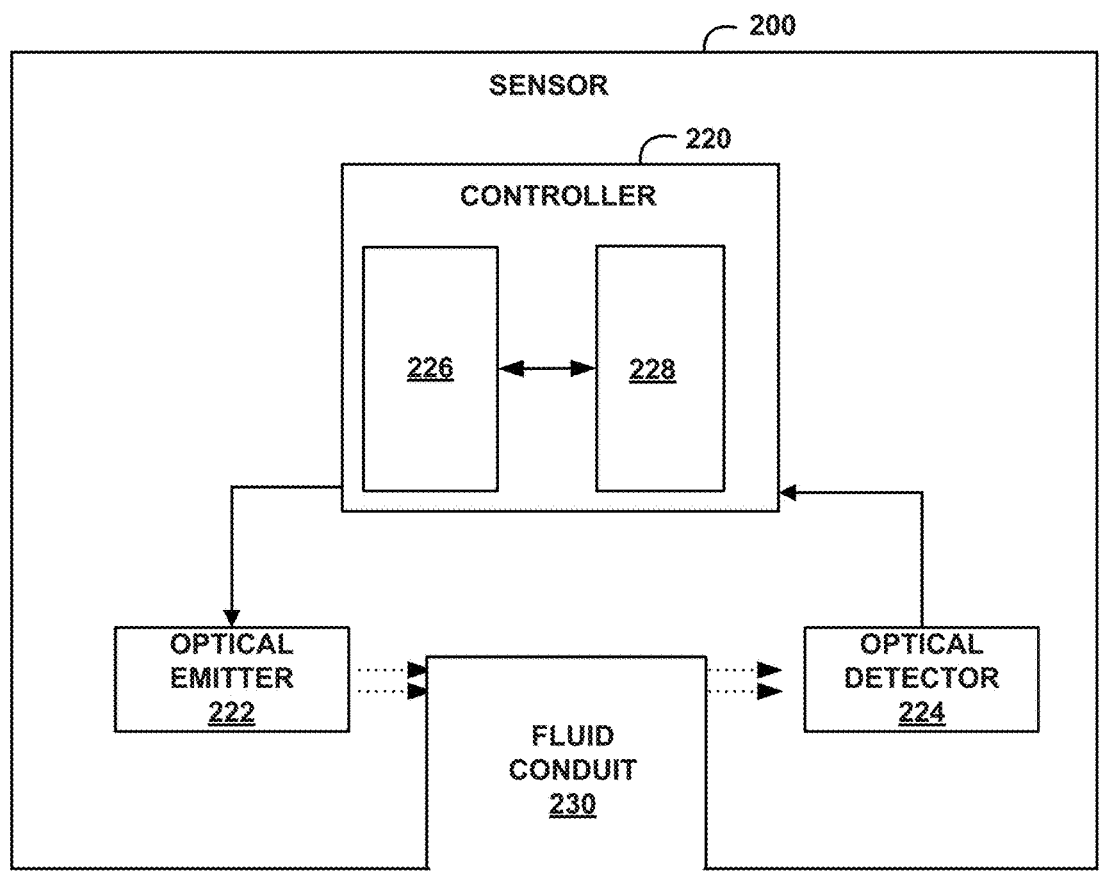
FIG. 2 is a block diagram of an example optical sensor that may be used in the system of FIG. 1.

In the example of FIG. 1, optical sensor 22 optically analyzes fluid flowing into fluid reservoir 20 via inlet 18, e.g., to determine a concentration of product liquid in a mixed fluid flow containing both product liquid and flushing liquid. FIG. 2 is a block diagram illustrating an example of an optical sensor 200 that may be used to optically analyze a fluid from system 10. Sensor 200 may be used as optical sensor 22 in system 10.

With reference to FIG. 2, sensor 200 includes a controller 220, one or more optical emitters 222 (referred to herein as "optical emitter 222"), and one or more optical detectors 224 (referred to herein as "optical detector 224"). Controller 220 (which may be the same as controller 32 in FIG. 1) includes a processor 226 and a memory 228. In operation, optical emitter 222 directs light into fluid (e.g., fluid containing product liquid, flushing liquid, and/or a combination of product liquid and flushing liquid) flowing through fluid conduit 230 and optical detector 224 detects fluorescent emissions generated by the fluid. The light directed into the fluid by optical emitter 222 may generate fluorescent emissions by exciting electrons of fluorescing molecules within the fluid, causing the molecules to emit energy (i.e., fluoresce) that can be detected by optical detector 224. For example, when light is directed into a fluid flowing through fluid conduit 16 (FIG. 1), electrons in molecules of product liquid within the fluid may excite, causing the molecules to fluoresce. In some examples, optical emitter 222 directs light at one frequency (e.g., ultraviolet frequency) into fluid flowing through fluid conduit 230 and causes fluorescing molecules to emit light energy at a different frequency (e.g., visible light frequency, a different ultraviolet frequency).

Memory 228 stores software and data used or generated by controller 220. For example, memory 228 may store data used by controller 220 to determine a concentration of one or more products within the fluid being monitored by sensor 200, such as a concentration of a product liquid or component thereof within a fluid being monitored by the sensor. In some examples, memory 228 stores data in the form of an equation that relates fluorescent emissions detected by optical detector 224 to a concentration of the one or more products.

Processor 226 runs software stored in memory 228 to perform functions attributed to sensor 200 and controller 220 in this disclosure. Components described as processors within controller 220, controller 30, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Optical emitter 222 includes at least one optical emitter that emits optical energy into a fluid present with fluid conduit 230. In some examples, optical emitter 222 emits optical energy over a range of wavelengths. In other examples, optical emitter 222 emits optical energy at one or more discrete wavelengths. For example, optical emitter 222 may emit at two, three, four or more discrete wavelengths.

In one example, optical emitter 222 emits light within the ultraviolet (UV) spectrum. Light within the UV spectrum may include wavelengths in the range from approximately 10 nm to approximately 400 nanometers. Light emitted by optical emitter 222 is directed into fluid within fluid conduit 230. In response to receiving the optical energy, fluorescing molecules (e.g., molecules present within the product liquid but not the flushing liquid) within the fluid may excite, causing the molecules to produce fluorescent emissions. The fluorescent emissions, which may or may not be at a different frequency than the energy emitted by optical emitter 222, may be generated as excited electrons within fluorescing molecules change energy states. The energy emitted by the fluorescing molecules may be detected by optical detector 224.

The specific wavelengths at which optical emitter 222 emits light may vary, e.g., depending on the type of fluorescing molecules expected to be present in product liquid 14. In some examples, optical emitter 222 emits light at a frequency of less than 350 nanometers (nm), such as less than 330 nm, or less than 300 nm. For example, optical emitter 222 may emit light in the frequency range of approximately 275 nm to approximately 335. The foregoing wavelengths are merely examples, however, and other wavelengths of light may be used.

Optical emitter 222 may be implemented in a variety of different ways within sensor 200. Optical emitter 222 may include one or more light sources to excite molecules within the fluid. Example light sources include light emitting diodes (LEDS), lasers, and lamps. In some examples, optical emitter 222 includes an optical filter to filter light emitted by the light source. The optical filter may be positioned between the light source and the fluid and be selected to pass light within a certain wavelength range. In some additional examples, the optical emitter includes a collimator, e.g., a collimating lens, hood or reflector, positioned adjacent the light source to collimate the light emitted from the light source. The collimator may reduce the divergence of the light emitted from the light source, reducing optical noise.

Sensor 200 also includes optical detector 224. Optical detector 224 includes at least one optical detector that detects fluorescent emissions emitted by excited molecules within fluid conduit 230. In some examples, optical detector 224 is positioned on a different side of fluid conduit 230 than optical emitter 222. For example, optical detector 224 may be positioned on a side of fluid conduit 230 that is offset approximately 90 degrees relative to optical emitter 222. Such an arrangement may reduce the amount of light that is emitted by optical emitter 222, transmitted through fluid within fluid conduit 230, and detected by optical detector 224. This transmitted light can potentially cause interference with fluorescent emissions detected by the optical detector.

In operation, the amount of optical energy detected by optical detector 224 may depend on the contents of the fluid within fluid conduit 230. If the fluid conduit contains a fluid solution that has certain properties (e.g., a certain concentration of product liquid), optical detector 224 may detect a certain level of fluorescent energy emitted by the fluid. However, if the fluid solution has different properties (e.g., a different concentration of product liquid), optical detector 224 may detect a different level of fluorescent energy emitted by the fluid. For example, if fluid conduit 230 is filled with a product liquid diluted to a first concentration by flushing liquid, optical detector 224 may detect a first magnitude of fluorescent emissions. However, if the fluid conduit is filled with a product liquid diluted with a second concentration of flushing liquid greater than the first concentration (e.g., such that the product liquid is more dilute), optical detector 224 may detect a second magnitude of fluorescent emissions that is less than the first magnitude.

Optical detector 224 may also be implemented in a variety of different ways within sensor 200. Optical detector 224 may include one or more photodetectors such as, e.g., photodiodes or photomultipliers, for converting optical signals into electrical signals. In some examples, optical detector 224 includes a lens positioned between the fluid and the photodetector for focusing and/or shaping optical energy received from the fluid.

It should be appreciated that although FIG. 2 illustrates one particular configuration of an optical sensor, other optical sensor configurations can be used without departing from the scope of the disclosure. For example, instead of positioning optical emitter 222 on a different side of fluid conduit 230 from optical detector 224, optical emitter 222 and optical detector 224 may be positioned to direct and receive light through a single, shared lens (e.g., ball lens) positioned on a face of the housing of sensor 200. When so configured, optical emitter 222 may direct light through the lens into a fluid flowing past the lens, causing the fluid to emit fluorescent emissions. These fluorescent emissions may be directed back through the lens to be detected by optical detector 224. Such an example optical sensor is described in U.S. patent application Ser. No. 14/039,683, entitled "MULTI-CHANNEL FLUOROMETRIC SENSOR AND METHOD OF USING SAME," which is commonly assigned with the present application and the entire contents of which are incorporated herein by reference.

Controller 220 controls the operation of optical emitter 222 and receives signals concerning the amount of light detected by optical detector 224. In some examples, controller 220 further processes signals, e.g., to determine a concentration of product liquid within the fluid passing through fluid conduit 230.

In one example, controller 220 controls optical emitter 222 to direct radiation into a fluid containing product liquid and further controls optical detector 224 to detect fluorescent emissions emitted by molecules of the product liquid within the fluid. Controller 220 then processes the light detection information to determine a concentration of the product liquid within the fluid and, if desired, also a concentration of flushing liquid within the fluid. Controller 220 can determine a concentration of the product liquid by comparing the magnitude of fluorescent emissions detected by optical detector 224 from a fluid having an unknown concentration of the product liquid to the magnitude of the fluorescent emissions detected by optical detector 224 from a fluid having a known concentration of the product liquid (e.g., a calibration fluid). In some examples, controller 220 determines concentrations of multiple products in a fluid based on the magnitude of fluorescent emissions detected by optical detector 224 at different wavelengths. For example, controller 220 may determine the concentration of different fluorescing molecules present within the product liquid and/or flushing liquid. This may be useful in applications where both the product liquid and the flushing liquid contain fluorescing molecules and the determined concentration of one or more of those fluorescing molecules can be used to resolve the fluorescent emissions associated with the product liquid from those of the flushing liquid.

In response to determining the concentration of a product in the fluid, processor 226 may compare the determined product concentration to one or more thresholds stored in memory 228, such as one or more concentration thresholds. Controller 220 may be informed of thresholds and the thresholds stored in memory 228, e.g., via user input at a user interface. Thresholds stored in memory 228 may act as a trigger point for controlling system 10 (FIG. 1).

With further reference to FIG. 1, for example, controller 32 may control system 10 until a concentration of product in the fluid flowing through fluid conduit 16 and into fluid reservoir 20 equals and/or exceeds a threshold value stored in memory. In one example, controller 32 controls pump 12 to pump flushing liquid such as water from source 14 toward fluid reservoir 20. The pressurized flushing fluid may push product liquid remaining in the fluid conduit into fluid reservoir 20. Fluid entering fluid reservoir 20 via inlet 18 may be substantially or entirely composed of product liquid at the start of the flushing process. Accordingly, as optical sensor 22 analyzes this fluid initially entering fluid reservoir 20, the fluid may emit fluorescent emissions corresponding to a product liquid concentration of approximately 100%. As the flushing fluid continues to flush fluid conduit 16, however, the flushing liquid may begin diluting the product liquid remaining in the fluid conduit such that fluid flowing into fluid reservoir 20 via inlet 18 comprises a mixture of product liquid and flushing liquid. When this fluid is optically analyzed by optical sensor 22, the fluid emits fluorescent emissions proportional to the concentration of product liquid and flushing liquid present in the fluid. In some examples, the concentration of fluorescing molecules present in the fluid flowing into fluid reservoir 20 may be comparatively high at the beginning of the flushing process but may decrease with time, for example, as product liquid is flushed out of fluid conduit 16 by a flushing fluid that is substantially devoid of fluorescing molecules and/or has a lesser concentration of fluorescing molecules than is present in the product liquid. At a certain point in the flushing process, the amount of residual product liquid being pushed into fluid reservoir 20 may diminish to a point where it is no longer beneficial to continue flushing. Controller 32 may make this determination based on concentration information determined by optical sensor 22 and threshold(s) stored in memory (e.g., memory 228 in FIG. 2).

The specific thresholds stored in memory 228 may depend, e.g., on the characteristics of the product liquid, the flushing liquid, and the configuration of system 10. For example, if the product liquid being processed in system 10 has a certain concentration of fluorescing molecules, memory 228 may store a concentration threshold value of a certain magnitude. By contrast, if the product liquid being processed in system 10 has a different concentration of fluorescing molecules, memory 228 may store a concentration threshold value of a different magnitude. During operation of system 10, controller 32 can control the components of the system to flush fluid conduit 16 with flushing liquid, e.g., until a concentration of product in the fluid flowing through the conduit exceeds a threshold (e.g., equals or falls below a concentration threshold). At this point, controller 32 may control system 10 to stop the flow of flushing liquid passing through fluid conduit 16 from being introduced into fluid reservoir 20. For example, controller 32 may stop pump 12 and/or manipulate valves within system 10 such that the fluid is not directed into fluid reservoir 20 but is instead directed to a different location, such as a waste drain.

The specific product concentration thresholds stored in memory can vary, for example, depending on the characteristics of the product flushing fluids and/or the quality of the product fluid being produced. For example, if yield recovery is of concern, memory 228 may store a concentration threshold of a certain magnitude whereas if product liquid adulteration is of concern, memory 228 may store a concentration threshold of a higher magnitude.

For yield recovery, the threshold stored in memory may be a value within a range from approximately 0 vol % product liquid (e.g., approximately 100 vol % flushing liquid) to approximately 25 vol % product liquid (e.g., approximately 75 vol % flushing liquid), such as a range from 0.1 vol % product liquid to 15 vol % product liquid, or from 0.5 vol % product liquid to 10 vol % product liquid. For product adulteration control, the threshold stored in memory may be a value within a range from approximately 100 vol % product liquid (e.g., approximately 0 vol % flushing liquid) to approximately 50 vol % product liquid (e.g., approximately 50 vol % flushing liquid), such as a range from 99 vol % product liquid to 75 vol % product liquid, or from 95 vol % product liquid to 80 vol % product liquid. When controller 32 determines that the concentration of product liquid in the fluid equals and/or falls below the threshold, the controller may stop pump 12 and/or close valves 26 and/or 28 to terminate the flushing process. It should be appreciated that the foregoing concentration thresholds are merely examples, and other concentration thresholds are both possible and contemplated.

During operation of system 10, controller 32 may determine a concentration of product in fluid flowing into fluid reservoir 20 and compare the determined concentration to a value stored in memory. Based on the comparison, controller 32 may adjust the flow of fluid (e.g., the flow of product liquid 14 and/or flushing liquid 24), e.g., until the determined concentration equals, is above, or below the target value. In instances in which controller 32 determines the concentration is below the value, controller 32 may electronically control the system, e.g., by stopping pump 12 or by decreasing the rate at which the pump pumps fluid, such as flushing fluid.

In some examples, system 10 may include one or more auxiliary sensors to monitor additional characteristics of fluid flowing through fluid conduit 16. The one or more auxiliary sensors may monitor optical or non-optical characteristics of the fluid flowing through the conduit and, in different examples, may or may not be integrated within an optical sensor (e.g., optical sensor 22, 200). In various examples, the one or more auxiliary sensors may include or be a temperature sensor, a pH sensor, and a turbidity sensor.

In one example, the one or more auxiliary sensors include an electrical conductivity sensor 23, which is illustrated as being integrated into optical sensor 22 in the example of FIG. 1. An electrical conductivity sensor 23 may be useful to detect any potential contaminants present in the fluid flowing through fluid conduit 16 since any contaminants may have an electrical conductivity different than that of the fluid that is supposed to be flowing through the conduit. If controller 32 determines that an electrical conductivity of the fluid flowing through fluid conduit 16 via electrical conductivity sensor 23 exceeds a threshold, controller 32 may stop pump 12 and/or manipulate valves within system 10 such that the fluid is not directed into fluid reservoir 20 but is instead directed to a different location. This can prevent the contaminated fluid from being dispensed into fluid reservoir 20. Controller 32 may also issue an alarm in such circumstances to notify operation personnel that the detected electrical conductivity of the fluid has exceeded a threshold.

Figure 3:
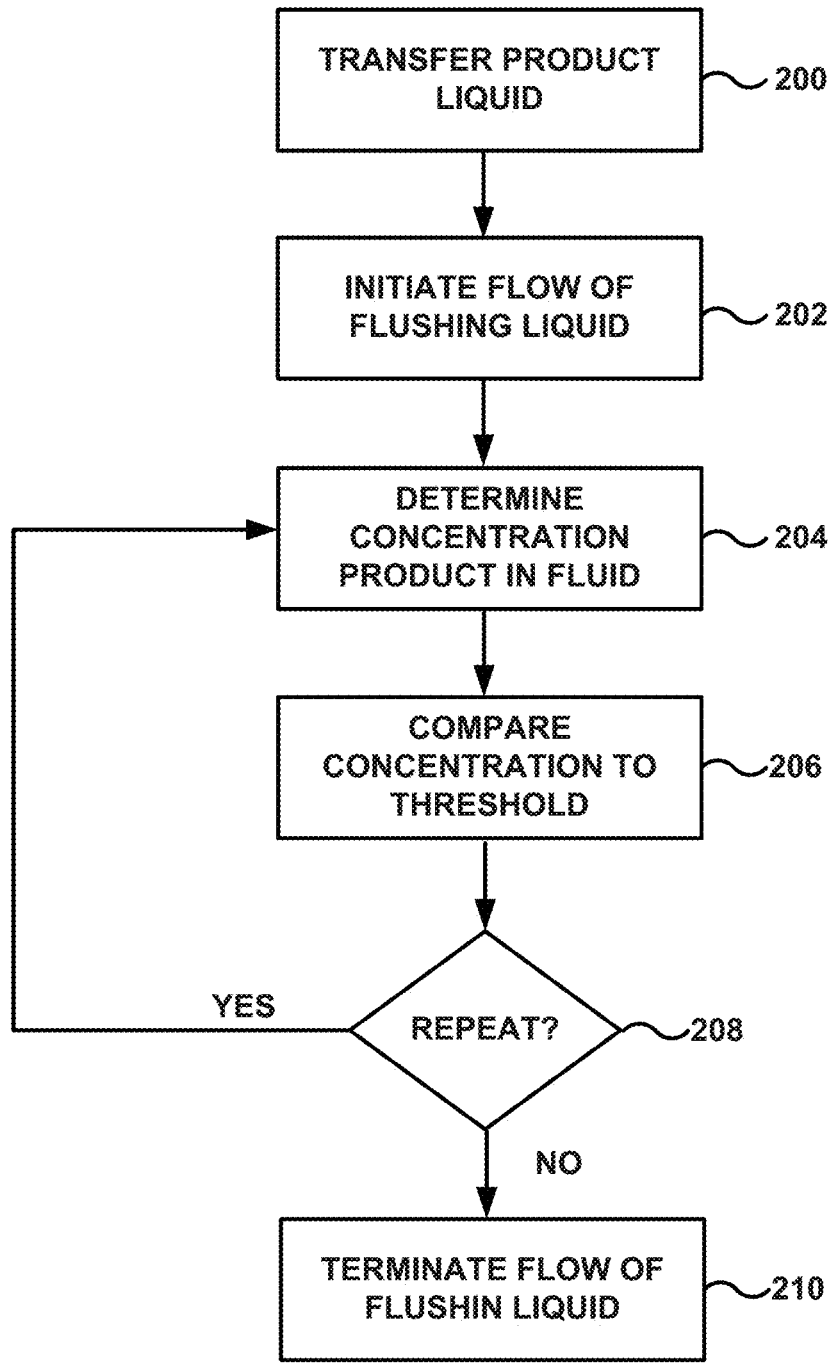
FIG. 3 is a block flow diagram of an example technique for performing a flushing operation.

FIG. 3 is a flow chart illustrating an example process for controlling a flushing operation. As shown, controller 32 initiates a transfer of a product liquid by opening valves 28 and/or 30 and activating pump 12 (200). In some examples, the product liquid contains fluorescing molecules that are naturally present in the liquid and are not added as a tracking agent. In some examples, the product liquid is a human-consumable liquid, such as juice, soup, a dairy product, a fermented beverage, or the like. Upon initiating the transfer, the product liquid moves from the product liquid source 14 to fluid reservoir 20 through fluid conduit 16. When a suitable volume of product liquid has been transferred to fluid reservoir 20, controller 32 may close valves 28 and/or 30 and deactivate pump 12. This can leave fluid conduit 16 partially or fully filled with residual product liquid that was received from source 14 but not delivered to reservoir 20.

After transferring the product fluid to fluid reservoir 20 (200), controller 32 initiates flushing (202). Controller 32 may open valves 28 and/or 30 and activate pump 12 to place the source of flushing liquid 24 in fluid communication with fluid reservoir 20. Pressurized flushing liquid flowing through fluid conduit 16 can displace residual product liquid and push the liquid into fluid reservoir 20.

In the technique of FIG. 3, optical sensor 22 receives fluid flowing through fluid conduit 16 and determines a concentration of a product in the fluid (204). Optical sensor 22 may direct light into the fluid and fluorescing molecules within the fluid may emit fluorescent energy in response to the light. Optical sensor 22 can detect the fluorescent energy and determine a concentration of product in the fluid based on the characteristics of the fluorescent energy. For example, optical sensor 22 may determine a concentration of the product liquid in the fluid by comparing a magnitude of the fluorescent energy and/or a wavelength of the fluorescent energy to calibration information stored in memory correlating different fluorescent energy characteristics to different product liquid concentrations.

After determining the concentration of product in the fluid flowing into fluid reservoir 20, controller 32 may compare the determined concentration to one or more concentration thresholds stored in memory (206). In different examples, the concentration thresholds may be preprogrammed into memory or may be received from a user via a user interface, e.g., at the start of the flushing process. Controller 32 may electronically control system 10 until the concentration of product in the fluid is equal to and/or below a concentration threshold stored in memory (208).

When controller 32 determines that the concentration of product (e.g., product liquid) in the fluid equals and/or falls below a concentration threshold, the controller can stop pump 12 and close valve 26 and/or 30 to terminate the flushing process (210).

The techniques described in this disclosure, including functions performed by a controller, control unit, or control system, may be implemented within one or more of a general purpose microprocessor, digital signal processor (DSP), application specific integrated circuit (ASIC), field programmable gate array (FPGA), programmable logic devices (PLDs), or other equivalent logic devices. Accordingly, the terms "processor" or "controller," as used herein, may refer to any one or more of the foregoing structures or any other structure suitable for implementation of the techniques described herein.

The various components illustrated herein may be realized by any suitable combination of hardware, software, and/or firmware. In the figures, various components are depicted as separate units or modules. However, all or several of the various components described with reference to these figures may be integrated into combined units or modules within common hardware, firmware, and/or software. Accordingly, the representation of features as components, units or modules is intended to highlight particular functional features for ease of illustration, and does not necessarily require realization of such features by separate hardware, firmware, or software components. In some cases, various units may be implemented as programmable processes performed by one or more processors or controllers.

Any features described herein as modules, devices, or components may be implemented together in an integrated logic device or separately as discrete but interoperable logic devices. In various aspects, such components may be formed at least in part as one or more integrated circuit devices, which may be referred to collectively as an integrated circuit device, such as an integrated circuit chip or chipset. Such circuitry may be provided in a single integrated circuit chip device or in multiple, interoperable integrated circuit chip devices.

If implemented in part by software, the techniques may be realized at least in part by a computer-readable data storage medium (e.g., a non-transitory computer-readable storage medium) comprising code with instructions that, when executed by one or more processors or controllers, performs one or more of the methods and functions described in this disclosure. The computer-readable storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), embedded dynamic random access memory (eDRAM), static random access memory (SRAM), flash memory, magnetic or optical data storage media. Any software that is utilized may be executed by one or more processors, such as one or more DSP's, general purpose microprocessors, ASIC's, FPGA's, or other equivalent integrated or discrete logic circuitry.

The following example may provide additional details about systems and techniques in accordance with this disclosure.

EXAMPLE 1

A variety of water-based product liquids were created and optically analyzed to evaluate the efficacy of using an optical sensor to monitor and control a flushing process. For the examples, liquid beverages were selected as the example product liquids and water was selected as the example flushing liquid. Each liquid beverage tested was diluted with water down to a concentration of 500 parts per million. The samples were subsequently fluorometrically analyzed by emitting light into the fluid samples and generating and detecting fluorescent emissions from the fluids.

Figure 4:
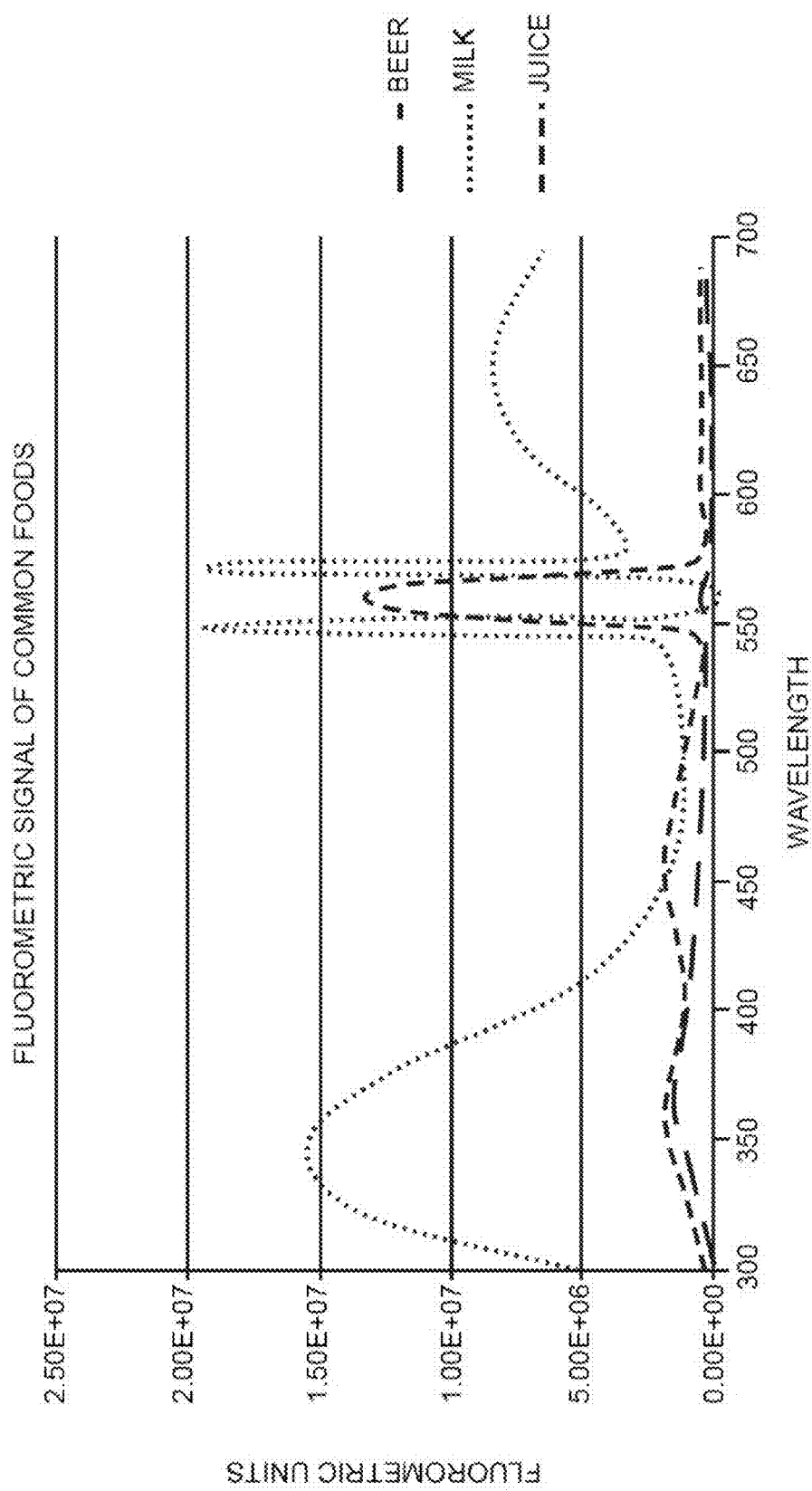
FIG. 4 is a plot showing example optical responses of different example product liquids.

FIG. 4 is a plot showing the optical response of the fluids when light at a wavelength ranging from 280 nanometers to 335 nanometers was emitted into the fluids. The x-axis of the plot is the wavelength of light emitted by the fluids in response to directing light into the fluids. The y-axis of the plot is the magnitude of light detected at each respective wavelength. The water used to dilute the example product liquids did not generate any fluorescent emissions in response to directing light into the fluid, indicating the optical response shown in FIG. 4 is from the product liquid alone and not the background water.

EXAMPLE 2

Figure 5:
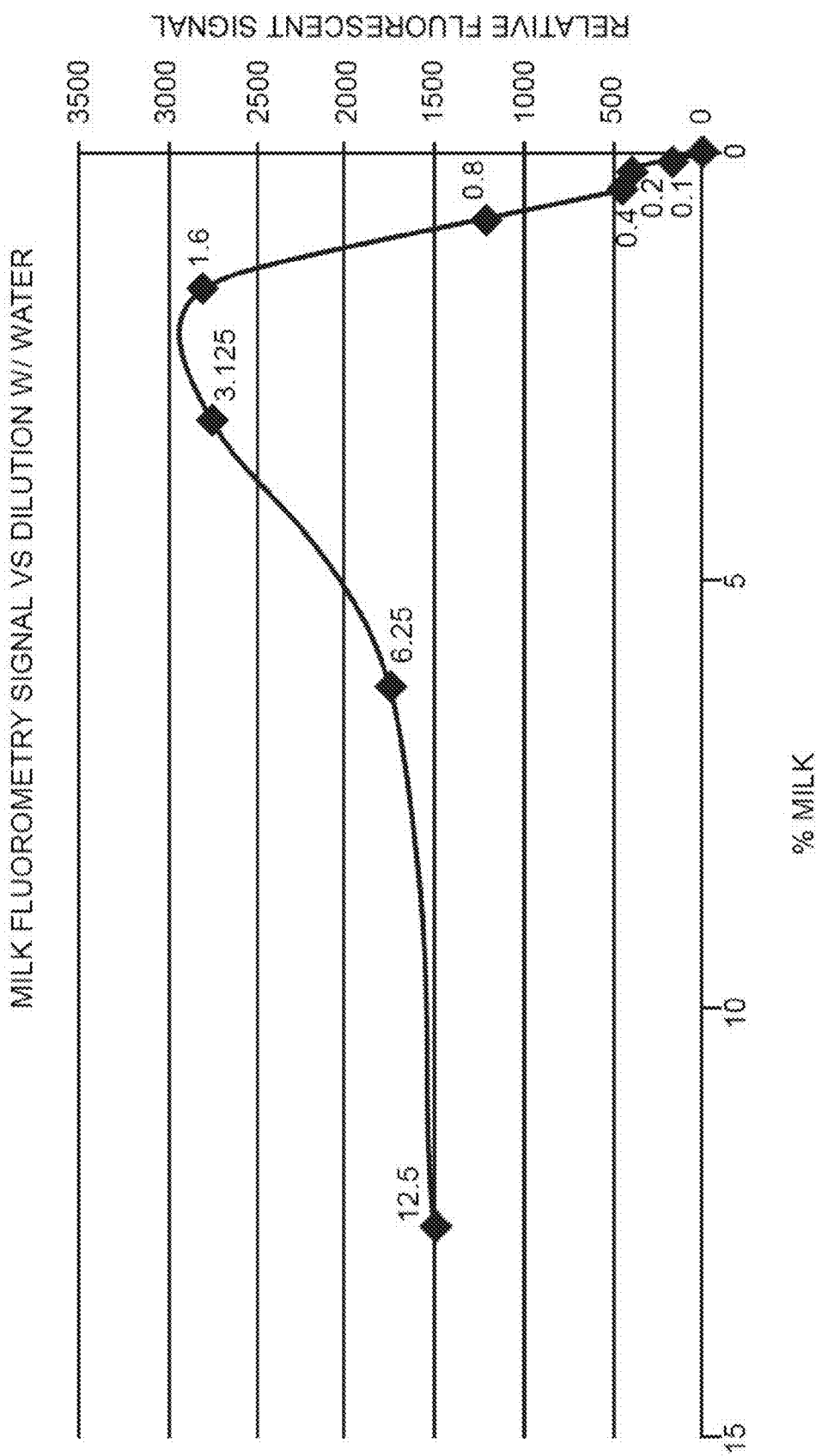
FIG. 5 is a plot showing example optical responses for several milk solutions having different concentrations of milk.

Several water-based solutions containing different concentrations of milk as the product liquid and water as the flushing liquid were created and optically analyzed to evaluate the efficacy of using an optical sensor to monitor a flushing process. The samples were subsequently fluorometrically analyzed by emitting light into the fluid samples and generating and detecting fluorescent emissions from the fluids. FIG. 5 is a plot showing the optical response of the milk solutions when light at a wavelength of 280 nanometers was emitted into the solutions. The x-axis of the plot is concentration of milk in the solutions by weight percent. The y-axis of the plot is the magnitude of light detected at 340 nm for the different solutions. For this example, the optical response of the milk solutions was linear from a concentration of approximately 1.6 percent down to approximately 0 percent, indicating that the concentration range may provide a good range for defining flushing end points.

EXAMPLE 3

A solution containing milk as the product liquid and water as the flushing liquid was created and optically analyzed. The solution started at 50 volume percent milk and 50 volume percent water and was subsequently diluted with increasing quantities of water. The solution was optically analyzed after each dilution to evaluate the efficacy of using an optical sensor to monitor a flushing process. FIG. 6 is a plot showing the optical response of the increasingly diluted milk solutions. The y-axis of the plot is the detected fluorometric signal from the milk, measured as the electrical signal from the optical detector in millivolts. The x-axis of the plot is time in minutes, which has been multiplied by five to adjust the scale of the plot.

The invention claimed is:
1. A method comprising:
   flushing a product liquid through a fluid conduit with a flushing liquid;
   fluorometrically analyzing a liquid flowing through the fluid conduit to cause molecules naturally present in the product liquid to fluoresce and thereby determine a concentration of the product liquid in the liquid flowing through the fluid conduit;
   comparing the determined concentration of the product liquid to a threshold value; and
   controlling the flushing liquid based on the determined concentration of the product liquid in the liquid flowing through the conduit,
   wherein controlling the flushing liquid based on the determined concentration of the product liquid comprises stopping a flow of the flushing liquid when the determined concentration crosses the threshold value.
2. The method of claim 1, wherein the product liquid comprises a human-consumable product.

3. The method of claim 2, wherein the product liquid comprises at least one of a dairy product, a juice, and a fermented beverage, and the flushing liquid consists essentially of water.

4. The method of claim 1, wherein the fluid conduit extends from an outlet of a discharge reservoir to an inlet of a receiving reservoir, and wherein fluorometrically analyzing liquid flowing through the fluid conduit comprises fluorometrically analyzing liquid flowing through the fluid conduit adjacent the inlet of the receiving reservoir.

5. The method of claim 1, wherein flushing the product liquid through the fluid conduit with the flushing liquid comprises flushing the product liquid with the flushing liquid such that the concentration of the product liquid decreases over time and a concentration of the flushing liquid increases over time.

6. The method of claim 1, wherein fluorometrically analyzing liquid flowing through the fluid conduit comprises directing light into the liquid flowing through the fluid conduit and thereby generating fluorescent emissions from the product liquid and detecting the fluorescent emissions emitted by the product liquid.

7. The method of claim 1, wherein controlling the flushing liquid based on the determined concentration of the product liquid further comprises at least one of adjusting a flow rate of the flushing liquid and opening or closing a valve through which the flushing liquid passes.

8. The method of claim 1, wherein the threshold value falls within a range from 0.5 volume percent product liquid to 10 volume percent product liquid.

9. The method of claim 1, further comprising analyzing an electrical conductivity of the liquid flowing through the fluid conduit and also controlling the flushing liquid based on the determined electrical conductivity of the liquid.

10. A method comprising:
    flushing a product liquid through a fluid conduit with a flushing liquid;
    fluorometrically analyzing a liquid flowing through the fluid conduit to determine a concentration of product liquid in the liquid flowing through the fluid conduit, wherein fluorometrically analyzing liquid flowing through the fluid conduit comprises directing light at a wavelength of less than approximately 350 nanometers (nm) into the liquid flowing through the fluid conduit and thereby generating fluorescent emissions from the product liquid and detecting the fluorescent emissions emitted by the product liquid at a wavelength greater than approximately 300 nm;
    comparing the determined concentration of the product liquid to a threshold value; and
    controlling the flushing liquid based on the determined concentration of the product liquid in the liquid flowing through the conduit,
    wherein controlling the flushing liquid based on the determined concentration of the product liquid comprises stopping a flow of the flushing liquid when the determined concentration crosses the threshold value.

11. The method of claim 10, wherein the product liquid comprises a human-consumable product.

12. The method of claim 11, wherein the product liquid comprises at least one of a dairy product, a juice, and a fermented beverage, and the flushing liquid consists essentially of water.

13. The method of claim 10, wherein the fluid conduit extends from an outlet of a discharge reservoir to an inlet of a receiving reservoir, and wherein fluorometrically analyzing liquid flowing through the fluid conduit comprises fluorometrically analyzing liquid flowing through the fluid conduit adjacent the inlet of the receiving reservoir.

14. The method of claim 10, wherein flushing the product liquid through the fluid conduit with the flushing liquid comprises flushing the product liquid with the flushing liquid such that the concentration of the product liquid decreases over time and a concentration of the flushing liquid increases over time.

15. The method of claim 10, wherein controlling the flushing liquid based on the determined concentration of the product liquid further comprises at least one of adjusting a flow rate of the flushing liquid and opening or closing a valve through which the flushing liquid passes.

16. The method of claim 10, wherein the threshold value falls within a range from 0.5 volume percent product liquid to 10 volume percent product liquid.

17. The method of claim 10, further comprising analyzing an electrical conductivity of the liquid flowing through the fluid conduit and also controlling the flushing liquid based on the determined electrical conductivity of the liquid.

* * * * *